United States Patent

O'Neil et al.

[11] Patent Number: 5,133,890
[45] Date of Patent: Jul. 28, 1992

[54] TRIAZOLE COMPOUNDS USEFUL AS METAL DEACTIVATORS

[75] Inventors: Robert M. O'Neil, Flixton, England; Paul Dubs, Marly, Switzerland

[73] Assignee: Ciba-Geigy Corporation, Ardsley, N.Y.

[21] Appl. No.: 713,943

[22] Filed: Jun. 12, 1991

[30] Foreign Application Priority Data

Jun. 13, 1990 [GB] United Kingdom ............... 9013142

[51] Int. Cl.$^5$ .......................................... C10M 133/44
[52] U.S. Cl. .................................. 252/51.5 R; 548/257
[58] Field of Search .................. 252/51.5 R, 68, 77; 548/257

[56] References Cited

U.S. PATENT DOCUMENTS

| | | | |
|---|---|---|---|
| 2,945,863 | 7/1960 | Buc et al. | 252/77 |
| 3,278,526 | 10/1966 | Louthan et al. | 260/239.3 |
| 3,849,433 | 11/1974 | Butula | 548/257 |
| 4,177,155 | 12/1979 | Popplewell et al. | 252/49.3 |
| 4,450,102 | 5/1984 | Lindstrom et al. | 252/542 |
| 4,522,785 | 6/1985 | D'Errico | 548/257 |
| 4,791,206 | 12/1988 | O'Neil | 548/257 |
| 4,897,086 | 1/1990 | Blain et al. | 548/269 |
| 5,032,300 | 7/1991 | O'Neil | 252/51.5 R |
| 5,076,946 | 12/1991 | Frankenfeld et al. | 548/257 |

FOREIGN PATENT DOCUMENTS

0006710 1/1980 European Pat. Off. .

Primary Examiner—Margaret Medley
Attorney, Agent, or Firm—Luther A. R. Hall

[57] ABSTRACT

A lubricant composition comprising a lubricating oil susceptible to degradation by a metal; and b) a metal deactivator having the formula I:

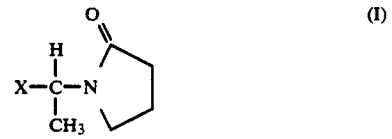

in which X formula II:

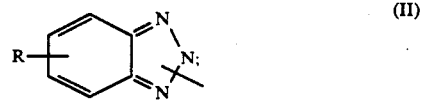

in which R is hydrogen or $C_1$–$C_4$ alkyl.

9 Claims, No Drawings

TRIAZOLE COMPOUNDS USEFUL AS METAL DEACTIVATORS

The present invention relates to new triazole compounds useful as metal deactivators, to compositions containing such compounds and functional fluids or fuels, and to a method of stabilizing functional fluids or fuels by adding said compounds thereto, as well as to a method of protecting metals in contact with such fluids or fuels.

In U.S. Pat. No. 4,450,102, there are described aqueous cleaning compositions containing, as active ingredient, a bis(N-2-pyrrolidonyl) sulphur-containing compound of formula:

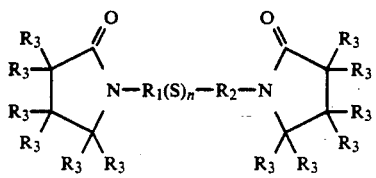

in which $R_1$ is $C_2$–$C_6$ alkylene, $R_2$ is $C_1$–$C_6$ alkylene; $R_3$ is hydrogen or $C_{1-3}$ alkyl; and n is 1 or 2.

There is also mention of the fact that one specific compound, namely, bis (2-[N-2-pyrrolidonyl]ethyl) sulphide, possesses copper corrosion inhibiting properties. A method of synthesising this compound is provided in U.S. Pat. No. 3,278,526. However, this method uses the highly toxic hydrogen sulphide as one reactant.

We have now found certain new oxo-pyrrolidinylethyl triazole compounds having excellent metal deactivation properties which can be synthesized by non-hazardous methods.

When lubricants are stabilized with triazole type metal deactivators problems may occur whenever the metal deactivator is too volatile. Due to the high temperatures to which the oil is subjected, especially in combustion engines or turbines, the concentration of the deactivator may decrease rapidly resulting in a decrease of protective activity Compounds of formula I are characterized by low volatilities in oils and may contribute to overcome the described problems.

Accordingly, the present invention provides compounds having the formula (I)

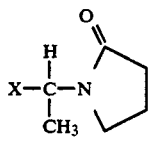

in which X is a group having the formula II or III:

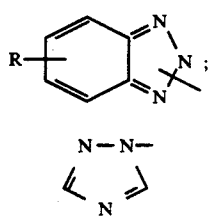

in which R is hydrogen or $C_1$–$C_4$ alkyl.

R is preferably hydrogen or methyl.

From formula II it is evident that the group of formula II can exist in two isomeric forms, IIA and IIB:

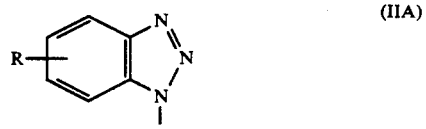

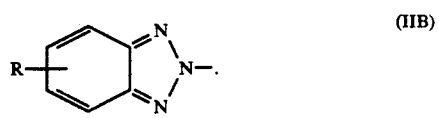

These isomers may be separated by methods known in the art. Preferably, however, the mixture of isomers is used for the desired purpose.

$C_1$–$C_4$ alkyl groups R are methyl, ethyl, n-propyl, isopropyl, n-butyl, isobutyl and tert.-butyl, especially methyl.

The compounds of formula I may be produced by the acid-catalysed addition of 1-vinyl-2-pyrrolidinone having the formula V:

to a triazole compound having the formula V, VI or VIA:

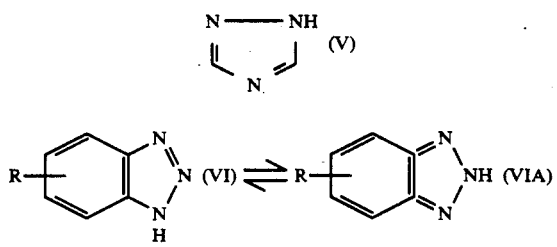

in which R has its previous significance.

Due to the tautomerism between formulae VI and VIA, two possible products may be obtained, represented by the above formulae II and IIA, respectively.

The addition reaction is conveniently performed in an inert solvent e.g. an aromatic solvent such as benzene, toluene or xylene; cyclohexane, carbon tetrachloride; or dioxan.

Optionally, the addition reaction may be conducted at ambient temperature although use of elevated temperature, conveniently the reflux temperature of any inert solvent, is preferred.

The amount of reactant of formula V used in preferably the stoichiometric amount required for complete reaction with the triazole of formula IV, to produce the desired product of formula I.

Acid catalysts for use in the process include e.g. sulphuric acid; phoshporic acid; acid ion-exchange resins, e.g. the commercially resin sold as Amberlyst 15; acid clays, e.g. bentonite, montmorillonite or Fuller's earth; or p-toluene sulphonic acid, p-toluene sulphonic acid being the preferred catalyst.

Isolation of the (isomeric) product(s) of formula I from the reaction mixture is conveniently effected by removal of catalyst and reaction solvent, followed by vacuum distillation of the residue.

The compounds of formula I are useful as metal deactivators in aqueous, partially aqueous and non-aqueous functional fluids or fuels.

The present invention, therefore, also provides compositions comprising a) a functional fluid or a fuel in contact with a metal, especially a ferrous metal or copper, and b) a metal deactivator having the formula I.

The compositions of the present invention preferably contain 0.001 to 5.0% especially 0.02 to 1.0% by weight of a compound of formula I, based on the weight of the functional fluid or fuel.

The functional fluid component of the compositions of the present invention may be non-aqueous, e.g. a lubricant having a mineral oil, poly-alpha olefin or synthetic carboxylic acid ester base; a hydraulic fluid based on mineral oils or phosphate esters; metal working fluids having a mineral oil base; engine coolant systems based on glycol/methanol or transformer or switch oils having a mineral oil base. Partially aqueous functional fluid components include hydraulic fluids based on aqueous polyglycol/polyglycol ether mixtures or glycol systems, or on oil-in-water or water-in-oil systems or engine coolant systems based on aqueous glycol. Completely aqueous functional fluid components include industrial cooling waters, aqueous air-conditioning systems, steam-generating systems, sea-water evaporator systems, sugar evaporator systems, irrigation systems, hydrostatic cookers, and aqueous closed-circuit heating or refrigerant systems.

Of particular interest as non-aqueous functional fluids or fuels are lubricants which are of mineral oil orgin or are synthetic oils, e.g. carboxylic acid esters, especially those intended for use at temperatures at or above 200° C.

Examples of carboxylic acid ester synthetic lubricants include those based on a diester of a dibasic acid and monohydric alcohol e.g. dioctyl sebacate or dinonyl adipate; or a triester of trimethylol propane and a monobasic acid or mixture of such acids e.g. trimethylol propane tripelargonate, trimethylol propane tricaprylate or mixtures of these; or a tetraester of pentaerythritol and a monobasic acid or a mixture of such acids e.g. pentaerythritol tetracaprylate; or on complex esters derived from monobasic acids, dibasic acids and polyhydric alcohols e.g. a complex ester derived from trimethylolpropane, caprylic acid and sebacic acid; or mixtures of one or more of such carboxylic acid esters.

Other synthetic lubricant bases are those described e.g. in "Schmiermittel-Taschenbuch" (Huethig Verlag, Heidelberg 1974), e.g. phosphates, glycols, polyglycols, polyalkylene glycols and poly-alpha olefins.

Mineral oil-based lubricant non-aqueous functional fluids are preferred.

Fuels may be the known hydrocarbons and mixtures thereof, for example for the use in internal combustion engines, and may be petrols, gasolines, diesel fuels and the like.

In addition to the compound of formula I, the non-aqueous or partly aqueous functional fluid compositions according to the present invention may contain, in order to improve the operating properties of the fluid, further additives. Such further additives include e.g. antioxidants, e.g. phenolic antioxidants, amine antioxidants, or other antioxidants, further metal deactivators, rust inhibitors, viscosity-index improvers, pour-point depressants, dispersants/surfactants, and anti-wear additives.

The compounds of formula I, when used alone, exert an excellent metal deactivating effect on working metal surfaces e.g. engine parts, especially of iron or, in particular copper, in contact with a non-aqueous functional fluid or fuel containing a metal degradant such as sulphur.

When, however, the organic material per se is the primary target for degradation e.g. when used in the presence of adventitious traces of metals such as iron or copper, and/or oxygen and/or hydroperoxides, then the compounds of formula I also exhibit stabilizing activity. It is very much preferred to use the compounds of formula I in combination with an antioxidant.

EXAMPLES OF PHENOLIC ANTIOXIDANTS

1. Alkylated Monophenols 2,6-Di-tert-butyl-4-methylphenol, 2,6-di-tert-butylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-i-butylphenol, 2,6-di-cyclopentyl-4-methylphenol, 2-($\beta$-methylcyclohexyl)-4,6-dimethylphenol, 2,6-di-octadecyl-4-methylphenol, 2,4,6-tricyclohexylphenol, 2,6-di-tert-butyl-4-methoxymethylphenol, o-tert-butylphenol.

2. Alkylated Hydroquinones 2,6-Di-tert-butyl-4-methoxyphenol, 2,5-di-tert-butyl-hydroquinone, 2,5-ditert-amyl-hydroquinone, 2,6-diphenyl-4-octadecyloxyphenol.

3. Hydroxylated Thiodiphenylethers 2,2'-Thio-bis-(6-tert-butyl-4-methylphenol), 2,2'-thio-bis-(4-octyl-phenol), 4,4'-thio-bis-(6-tert-butyl-3-methylphenol), 4,4'-thio-bis-(6-tert-butyl-2-methylphenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-($\alpha$-methylcyclohexyl)-phenol), 2,2'-methylene-bis-(4-methyl-6-cyclohexylphenol), 2,2'-methylene-bis-(6-nonyl-4-methylphenol), 2,2'-methylene-bis(4,6-di-tert-butylphenol), 2,2'-ethylidene-bis-(4,6-di-tert-butylphenol), 2,2'-ethylidene-bis-(6-tert-butyl-4- or -5-isobutylphenol), 2,2'-methylene-bis-(6-($\alpha$-methylbenzyl-4-nonyl-phenol), 2,2'-methylene-bis-(6-($\alpha,\alpha$-dimethylbenzyl)-4-nonylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)-butane, 2,6-di-(3-tert-butyl-5-methyl-2-hydroxy-benzyl)-4-methylphenol-1,1,3-tris-(5-tert-butyl-4-hydroxy-2-methylphenyl)-3-n-dodecyl)-mercaptobutane, ethyleneglycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethylbenzene, bis-(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethylbenzyl)dithiolterephthalate, 1,3,5-tris-(3,5-di-tert-butyl-4-hydroxybenzyl)-isocyanurate, 1,3,5-tris-(4-tert-butyl-3-hydroxy-2,6-dimethylbenzyl)-isocya nurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols

4-Hydroxy-lauric acid anilide, 4-hydroxy-stearic acid anilide, 2,4-bis-octylmercapto-6-(3,5-di-tert-butyl-4-hydroxyanilino)-s-triazine, N-(3,5-di-tert-butyl-4-hydroxyphenyl)-carbamic acid octyl ester.

7. Esters of β-(3,5-Di-tert-butyl-4-hydroxyphenol)-propionic acid with mono- or polyhydric alcohols, for example with methanol, diethyleneglycol, octadecanol, triethyleneglycol, 1,6-hexanediol, pentaerythritol, neopentylglycol, tris-hydroxyethyl-isocyanurate, thiodiethyleneglycol, bis-hydroxyethyl-oxalic acid diamide.

8. Esters of β-(5-tert-butyl-4-hydroxy-3-methylphenyl)-propionic acid with mono- or polyhydric alcohols, for example with methanol, diethyleneglycol, octadecanol, triethyleneglycol, 1,6-hexanediol, pentaerythritol, neopentylglycol, tris-hydroxyethyl-isocyanurate, thiodiethyleneglycol, di-hydroxyethyl-oxalic acid diamide.

9. Amides of β-(3,5-Di-tert-butyl-4-hydroxyphenyl)-propionic acid for example

N,N'-Bis-(3,5-di-tert-butyl-4-hydroxyphenylpropionyl)-hexamet hylene-diamine, N,N'-bis(3,5-di-tert-butyl-4-hydroxyphenylpropionyl)-tri-met hylene-diamine, N,N'-bis-(3,5-di-tert-butyl-4-hydroxyphenyl-propionyl)-hydraz ine.

EXAMPLES OF AMINE ANTIOXIDANTS

N,N'-Di-isopropyl-p-phenylenediamine, N,N'-di-sec.-butyl-p-phenylenediamine, N,N'-bis(1,4-dimethyl-pentyl)-p-phenylenediamine, N,N'-bis(1-ethyl-3-methylpentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di(naphthyl-2-)-p-phenylenediamine, N-isopropyl-N'-phenyl-p-phenylenediamine, N-(1,3-dimethyl-butyl)-N'-phenyl-p-phenylenediamine, N-(1-methyl-heptyl)-N'-phenyl-p-phenylenediamine, N-cyclohexyl-N'-phenyl-p-phenylene-diamine, 4-(p-toluene-sulfonamido)-diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylamino-phenol, 4-nonanoylamino-phenol, 4-dodecanoylamino-phenyl, 4-octadecanoylamino-phenol, di-(4-methoxyphenyl)-amine, 2,6-di-tert-butyl-4-dimethylamino-methyl-phenol, 2,4'-diamino-diphenylmethane, 4,4'-diamino-diphenylmethane, N,N,N',N'-tetramethyl-4,4'-diamino-diphenylmethane, 1,2-di-(phenylamino)-ethane, 1,2-di-[2-methylphenyl)-amino]-ethane, 1,3-di-(phenylamino)-propane, (o-tolyl)-biguanide, di-[4-1',3'-dimethyl-butyl)-phenyl]amine, tert-octylated N-phenyl-1-naphthylamine, mixture of mono-and dialkylated tert-butyl-/tert-octyldiphenylamines, 2,3-dihydro-3,3-dimethyl-4H-1,4-benzothiazine, phenothiazine, n-allylphenothiazine.

EXAMPLES OF OTHER ANTIOXIDANTS

Aliphatic or aromatic phosphites, esters of thiodipropionic acid or of thiodiacetic acid, or salts of dithiocarbamic or dithiophosphoric acid.

Examples of further metal deactivators for copper, are:

Further triazoles, benzotriazoles and derivatives thereof, tolutriazole and derivatives thereof, 2-mercaptobenzothiazole, 2,5-dimercaptothiadiazole, 5,5'-methylene-bis-benzotriazole, 4,5,6,7-tetrahydrobenzotriazole, salicylidene-propylenediamine and salicylaminoguanidine and salts thereof.

Examples of rust inhibitors are:

a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amides, 4-nonyl-phenoxy-acetic acid, and the rust inhibitors described in European Patent Specification 89810524.

b) Nitrogen-containing compounds, e.g. i) primary, secondary or tertiary aliphatic or cycloaliphatic amines and amine-salts of organic and inorganic acids, e.g. oil-soluble alkylammonium carboxylates, and ii) heterocyclic compounds, e.g. substituted imidazolines and oxazolines.

c) Phosphorus-containing compounds, e.g. Amine salts of phosphonic acid or phosphoric acid partial esters, zinc dialkyldithio phosphates.

d) Sulfur-containing compounds, e.g. Barium-dinonylnaphthalene-n-sulfonates, calcium petroleum sulfonates.

Examples of viscosity-index improvers are:

Polyacrylates, polymethacrylates, vinylpyrrolidone/methacrylate co-polymers, polyvinylpyrrolidones, polybutenes, olefin-copolymers, styrene/acrylate co-polymers and polyethers.

Examples of pour-point depressants are:

Polymethacrylates and alkylated naphthalene derivatives.

Examples of dispersants/surfactants are:

Polybutenylsuccinic acid-amides or -imides, polybutenylphosphonic acid derivatives, basic magnesium-, calcium-, and bariumsulfonates and -phenolates.

Examples of anti-wear additives are:

Sulfur- and/or phosphorus- and/or halogen-containing compounds e.g. sulfurised vegetable oils, tritolyl-/phosphate, chlorinated paraffins, alkyl- and aryldi- and tri-sulfides, triphenylphosphorothionate.

When the non-aqueous functional fluid or fuel is one which is liable to degrade by oxidation, e.g. a lubricant composition, one particular preferred class of co-additives for use in conjunction with the compounds of formula I, comprises phenolic or amine-type antioxidants, especially amine-type antioxidants e.g. diphenylamine, octylated diphenylamine, N-phenyl-1-naphthylamine and N-(octylated-phenyl)-1-naphthylamine, with which the compounds of formula I exhibit a synergistic effect.

In addition to the metal deactivator of formula I, the completely aqueous compositions according to the present invention may contain, in order to improve their operating properties, further additives, e.g. further metal deactivators, corrosion- or rust inhibitors, dispersing and/or threshold agents, precipitating agents, oxygen scavengers, sequestering agents, anti-foaming agents and biocides.

Corrosion inhibitors which may be used are, for example, water soluble zinc salts; phosphates; polyphosphates; phosphonic acids and their salts, for example, acetodiphosphonic acid, nitrilotris methylene phosphonic acid and methylamine dimethylene phosphonocarboxylic acids and their salts, for example, those described in German Offenlegungsschrift 2632774, hydroxyphosphonoacetic acid, 2-phosphonobutane-1,2,4-tricarboxylic acid and those disclosed in GB 1572406; nitrates, for example sodium nitrate; nitrites e.g. sodium nitrite; molybdates e.g. sodium molybdate; tungstates; or silicates e.g. sodium silicate. Further metal deactivators are benzotriazole, bis-benzotriazole or copper deactivating benzotriazole or tolutriazole derivatives or their Mannich base derivatives; N-acyl sarcosines; N-acylimino diacetic acids; ethanolamines, fatty amines; and polycarboxylic acids, for example, polymaleic acid and polyacrylic acid, as well as their respective alkali metal salts, copolymers of acrylic acid and hydroxyalkylated acrylic acid, and substituted derivatives of polymaleic and polyacrylic acids and their copolymers. Moreover, in such completely aqueous systems, the triazole metal deactivator of formula I used according to the invention may be used in conjunction with dispersing and/or threshold agents e.g. polymerised acrylic acid (or its salts), phosphino-polycarboxylic acids (as described and claimed in British Patent 1458235), the cotelomeric compounds described in European Patent Application No. 150706, hydrolysed polyacrylonitrile, polymerised methacrylic acid and its salts, polyacrylamide and copolymers thereof from acrylic and methacrylic acids, lignin sulphonic acid and its salts, tannin, naphthalene sulphonic acid/formaldehyde condensation products, starch and its derivatives, cellulose, acrylic acid/lower alkyl hydroxyacrylate copolymers e.g. those described in U.S. Pat. No. 4,029,577, styrene/maleic anhydride copolymers and sulphfonated styrene homopolymers e.g. those described in U.S. Pat. No. 4,374,733 and combinations thereof. Specific threshold agents, such as for example, 2-phosphonobutane-1,2,4-tri-carboxylic acid, acetodiphosphonic acid, hydrolysed polymaleic anhydride and its salts, alkylphosphonic acid, hydroxyphosphonoacetic acid 1-aminoalkyl-1,1-diphosphonic acids and their salts, and alkali metal poly-phosphates, may also be used.

Precipitating agents such as alkali metal orthophosphates, carbonates; oxygen scavengers such as alkali metal sulphites and hydrazines; sequestering agents such as nitrilotriacetic acid and its salts; antifoaming agents such as silicones e.g. polydimethylsiloxanes, distearylsebacamides, distearyl adipamide and related products derived from ethylene oxide and/or propylene oxide condensations, in addition to fatty alcohols, such as capryl alcohols and their ethylene oxide condensates; and biocides e.g. amines, quaternary ammonium compounds, chlorophenols, sulphur-containing compounds such as sulphones, methylene bis thiocyanates and carbamates, isothiazolones, brominated propionamides, triazines, phosphonium compounds, chlorine and chlorine-release agents and organometallic compounds such as tributyl tin oxide, may be used.

The following Examples further illustrate the present invention. Parts and percent are by weight unless otherwise stated.

EXAMPLE 1

[1-(2-oxo-1-pyrrolidinyl)ethyl]tolyltriazole

A mixture of tolytriazole (26.6 g; 0.2 moles), 1-vinyl-2-pyrrolidinone (22.2 g; 0.2 moles) and para toluene sulphonic acid (0.14 g) is heated in toluene (200 ml), under reflux, for 7 hours. The mixture is then cooled to ambient temperature and washed with 5% sodium bicarbonate solution (50 ml), water (2×50 ml) and finally, dried over anhydrous magnesium sulphate. The dried extract is filtered and then evaporated to yield a yellow oil. Short-path distillation of the crude product yields a pale yellow viscous oil (34.9 g; 71%), bp 175°/0.05 mbar.

Analysis Found: C, 63.42%; H, 6.87%; N, 23.11%. $C_{13}H_{16}N_4O$ requires: C, 63.91%; H, 6.60%; N, 22.94%.

EXAMPLE 2

[1-(2-oxo-1-pyrrolidinyl)ethyl]benzotriazole

This product is synthesised, in 64% yield, from benzotriazole and 1-vinyl-2-pyrrolidinone by the same method described in Example 1. The product distils at 180°/0.05 mbar and solidifies, on standing, to yield a white solid mp 77°-9° C.

Analysis Found: C, 62.55%; H, 6.13%; N, 24.37%. $C_{12}H_{14}N_4O$ requires: C, 62.59%; H, 6.13%; N, 24.33%.

EXAMPLE 3

[1-(2-oxo-1-pyrrolidinyl)ethyl]1,2,4-triazole

This product is synthesised, in 63% yield, from 1,2,4-triazole and 1-vinyl-2-pyrrolidinone by a similar method described in Example 1. On account of the higher water solubility of this product, ethyl acetate (3×50 ml) is used to extract it from the aqueous phase during washing. The product distils as a pale yellow oil, 150°/0.05 mbar.

Analysis Found: C, 52.77%; H, 7.18%; N, 31.54%. $C_8H_{12}N_4O$ requires: C, 53.32%; H, 6.71%; N, 31.10%,

EXAMPLES 4 AND 5

(Modified) ASTM D-130 Copper Strip Test

A 0.05% solution of the test compound is prepared in a turbine quality mineral oil of viscosity 26.2 mm²/s at 40° C., 4.8 mm²/s at 100° C. and S-content of 0.54% in which 50 ppm of elemental sulphur has been dissolved.

A copper strip (60×10×1 mm) is polished with 100 grade silicon carbide grit which has been picked up on cotton wool wetted with petroleum ether. The polished strip is then immediately totally immersed in the prepared solution, which is maintained at 100° C. for 2 hours. After this time, the strip is removed, washed with petroleum ether, dried and its colour is compared with those of the ASTM D130 Copper Strip Corrosion Standard Chart.

The results are summarised in the following Table 1:

TABLE 1

| Modified ASTM D-130 Copper Strip Test | | |
|---|---|---|
| Example | Test Compound | ASTM D-130 rating |
| — | blank (no additive) | 3B |
| 4 | product of Example 1 | 1A |
| 5 | product of Example 2 | 1B |

A rating of 1 denotes a slight tarnish; a rating of 2 a moderate tarnish; a rating of 3 a dark tarnish; and a rating of 4 severe corrosion. Letters A, B, C and D are used to indicate shadings within the broad numerical values.

The results in the Table demonstrate the excellent copper deactivation test results achieved in a non-aqueous functional fluid or fuel using the compounds according to the present invention.

EXAMPLE 6 to 9

Rotary Bomb Oxidation Test ASTM D-2272

A 0.05% solution of the test compound is prepared in a turbine quality mineral oil of viscosity 26.2 $mm^2/s$ at 40° C., 4.8 $mm^2/s$ at 100° C. and S-content of 0.54% which may also contain either a phenolic or aminic antioxidant.

The time taken for the oxygen pressure in the bomb to drop more than 175 kPa below the maximum pressure is recorded.

The results obtained are set out in the following Table 2:

TABLE 2

| | ASTM D-2272 Rotary Bomb Oxidation Test | | | RBOT mins. |
|---|---|---|---|---|
| | Test Compounds | | | |
| Example | Compound of invention | Antioxidant A | Antioxidant B | to 175 kPa pressure drop |
| — | none (base oil only) | — | — | 25 mins |
| — | none | 0.10% | — | 65 mins |
| — | none | — | 0.10% | 85 mins |
| 6 | Product of Example 1 | 0.10% | — | 215 mins |
| 7 | Product of Example 1 | — | 0.10% | 325 mins |
| 8 | Product of Example 2 | 0.10% | — | 355 mins |
| 9 | Product of Example 2 | — | 0.10% | 440 mins |

Antioxidant A is a commercially available mixture of tert-butylated phenols: Irganox L 108 ® (Ciba-Geigy).

Antioxidant B is a commercially available di-tert-octylated diphenylamine: Irganox L 57 ® (Ciba-Geigy).

The results in the Table indicate that when used in combination with an amine or phenolic antioxidant, the metal deactivator compounds of formula I impart excellent antioxidant properties to the lubricant composition.

EXAMPLES 10 TO 18

Solutions of test compounds of formula (I) are prepared in water containing 0.132 g/l $MgSO_4.7H_2O$ and 0.663 g/l $CaCl_2.6H_2O$ (water as used in DIN 51360 test).

A piece of copper foil (20×50×0.1 mm) is cleaned by rubbing it with cotton wool soaked with water and powdered pumice, dried and weighed. It is then fully immersed in 75 ml of the solution so prepared contained in a 100 ml bottle fitted with a screw cap. The bottle is then placed for 24 hours in an oven maintained at 70° C. At the end of this time, the strip is removed, then immersed for 15 seconds in 5N hydrochloric acid at 20° C., washed, dried and reweighed. The results are summarised in Table 3:

TABLE 3

| Example | | Concentration | Weight Loss |
|---|---|---|---|
| — | Blank (no additive) | — | 6.2 mg |
| 10 | Product of Example 1 | 500 ppm | 0.1 mg |
| 11 | | 250 ppm | 0.2 mg |
| 12 | | 125 ppm | 0.1 mg |
| 13 | | 62.5 ppm | 0.4 mg |
| 14 | Product of Example 2 | 500 ppm | 0.4 mg |
| 15 | | 250 ppm | 0.3 mg |
| 16 | | 125 ppm | 0.3 mg |
| 17 | | 62.5 ppm | 0.2 mg |
| 18 | Product of Example 3 | 500 ppm | 0.4 mg |

The results demonstrate the excellent activity of the compounds of the invention as metal deactivators in aqueous solution.

EXAMPLE 19

Solutions of the test compound of Example 1 are prepared in a commercially available antifreeze concentrate comprising ethylene glycol, sodium nitrite, sodium nitrate, sodium borate, sodium silicate and sodium benzoate but containing no metal deactivator.

The concentrate thus prepared is then diluted to $33\frac{1}{3}$% v/v with ASTM water (100 ppm each of $SO_4^{2-}$, $Cl^-$ and $HCO_3^-$ as sodium salts) and the resulting solution is subjected to the ASTM D-1384 test. The test conditions are 88° C.±2° for 336 hours and an oxygen flow rate of 100 ml/min.

The test results are summarised in the Table 4 below. The data refer to weight losses in g/sq.in.(1 g/sq.in = $1.55 \cdot 10^{-3}$ $g/mm^2$). Negative values denote a weight gain.

TABLE 4

| | | Metal | | | | |
|---|---|---|---|---|---|---|
| Example | Test Formulation | Copper | Solder | Brass | Steel | Aluminium |
| A | Commercially available AF*) concentrate containing no metal deactivator | 1.51 | 2.49 | 1.00 | −1.28 | −3.37 |
| 19 | Commercially available AF*) concentrate of formulation A but containing 0.30% by weight of the product of Example 1 | 0.11 | 0.02 | 0.02 | −0.19 | −0.34 |

*)AF = anti-freeze

The results of these tests demonstrate the excellent multi-metal protection provided by a compound of the invention when used in an antifreeze formulation.

We claim:

1. A lubricant composition comprising
   (a) a major amount of lubricating oil in contact with a metal; and
   (b) a minor effective amount of a metal deactivator compound of formula I

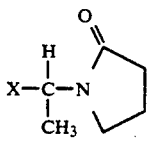

in which X is formula II:

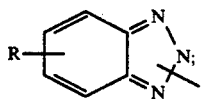

in which R is hydrogen or $C_1$–$C_4$ alkyl.

2. The composition according to claim 1 wherein the metal is a ferrous metal or copper.

3. The composition according to claim 1 wherein the amount of the compound of formula I present is from 0.001 to 5% by weight, based on the weight of the lubricating oil.

4. The composition according to claim 3 wherein the amount of the compound of formula I present is from 0.02 to 1.0% by weight, based on the weight of the lubricating oil.

5. A composition according to claim 1 where the lubricating oil is of mineral origin.

6. The composition according to claim 1 wherein the composition also include one or more of an antioxidant, a further metal deactivator, a rust inhibitor, a viscosity-index improver, a pour-point depressant, a dispersant-/surfactant and an anti-wear additive.

7. The composition according to claim 6 wherein the antioxidant is an amine antioxidant.

8. The composition according to claim 7 wherein the amine antioxidant is diphenylamine, octylated diphenylamine, N-phenyl-1-naphthylamine or N-(octylated phenyl)-1-naphthylamine.

9. The composition according to claim 1 where in R is hydrogen or methyl.

* * * * *